(12) United States Patent
Sung et al.

(10) Patent No.: US 7,716,986 B2
(45) Date of Patent: May 18, 2010

(54) ACOUSTIC WAVE SENSING DEVICE INTEGRATED WITH MICRO-CHANNELS AND METHOD FOR THE SAME

(75) Inventors: Po-Hsun Sung, Jhudong Township, Hsinchu County (TW); Wen-Wang Ke, Jhudong Township, Hsinchu County (TW); Nai-Hao Kuo, Jhudong Township, Hsinchu County (TW); Yu-Sheng Hsieh, Jhudong Township, Hsinchu County (TW)

(73) Assignee: Industrial Technology Research Institute, Hsinchu County (TW)

( * ) Notice: Subject to any disclaimer, the term of this patent is extended or adjusted under 35 U.S.C. 154(b) by 932 days.

(21) Appl. No.: 11/326,388

(22) Filed: Jan. 6, 2006

(65) Prior Publication Data
US 2007/0000327 A1    Jan. 4, 2007

(30) Foreign Application Priority Data
Jul. 1, 2005    (TW) .............................. 94122468 A (51) Int. Cl.
*G01N 29/04*    (2006.01)
*H01L 41/00*    (2006.01)
(52) U.S. Cl. .............................. 73/584; 73/590; 73/332; 310/313 B; 310/334
(58) Field of Classification Search .................... 73/584, 73/590, 599, 602, 632, 61.75; 310/313 R, 310/313 A, 313 B, 311, 334
See application file for complete search history.

(56) References Cited
U.S. PATENT DOCUMENTS
4,296,348 A * 10/1981 Toda .......................... 310/334
(Continued)

FOREIGN PATENT DOCUMENTS
CN       1173557 A       11/2005
(Continued)

OTHER PUBLICATIONS
Luginbuhl et al., "Microfabricated Lamb wave device based on PZT Sol-Gel thin film for mechanical transport of solid particles and liquids," Dec. 1997, Journal of Microelectromechanical System, vol. 6, No. 4, pp. 337-346.
(Continued)

*Primary Examiner*—J M Saint Surin
(74) *Attorney, Agent, or Firm*—Rabin & Berdo, P.C.

(57) ABSTRACT

An acoustic wave sensing device integrated with micro-channels and a method for the same are described. The present invention uses a piezoelectric substrate with a thinner portion serving as a sensing area and formed via a micromaching or chemical process. An inter-digital transducer (IDT) is located on the thinner portion to produce flexural plate waves (FPW). The micro-channels can be formed together with the thinner portion via the same manufacturing process, or integrated into the piezoelectric substrate via linkage. In the present invention, a novel manufacturing process and design are proposed for fabrication of the acoustic wave sensing devices with a good piezoelectric characteristic, a stable temperature compensation property, and a robust structure. Thereby, the techniques of flexural plate waves can be applied for liquid sensors. In this way, the drawbacks of the conventional acoustic wave sensing devices, such as poor piezoelectric properties and fragile film structures, are removed.

28 Claims, 8 Drawing Sheets

U.S. PATENT DOCUMENTS

| | | |
|---|---|---|
| 5,212,988 A | 5/1993 | White et al. |
| 5,306,644 A * | 4/1994 | Myerholtz et al. .......... 436/149 |
| 6,106,149 A * | 8/2000 | Smith .......................... 374/31 |
| 6,163,099 A * | 12/2000 | Kadota et al. ........... 310/313 A |
| 6,171,378 B1 * | 1/2001 | Manginell et al. ............. 96/143 |
| 6,189,367 B1 * | 2/2001 | Smith et al. ................ 73/19.03 |
| 6,190,035 B1 * | 2/2001 | Smith .......................... 374/31 |
| 6,378,370 B1 | 4/2002 | Haskell et al. |
| 6,445,265 B1 * | 9/2002 | Wright ....................... 333/193 |
| 6,455,265 B1 | 9/2002 | Serres |
| 6,688,158 B2 | 2/2004 | Cunningham et al. |
| 2001/0054305 A1 | 12/2001 | Banda et al. |

FOREIGN PATENT DOCUMENTS

| | | |
|---|---|---|
| JP | 2005-117364 A | 4/2005 |

OTHER PUBLICATIONS

Cai et al, "Vapor recognition with an integrated array of polymer-coated flexural plate wave sensors," 2000, Sensors and Actuators B 62, pp. 121-130.

* cited by examiner

ACOUSTIC WAVE SENSING DEVICE INTEGRATED WITH MICRO-CHANNELS AND METHOD FOR THE SAME

BACKGROUND OF THE INVENTION

1. Field of the Invention

The present invention is related to an acoustic wave sensing device integrated with micro-channels, and more particularly to an acoustic wave sensing device that has a substrate made of a piezoelectric material and is processed by techniques of micromaching. The sensing device of the present invention can be used for analysis of specific ingredients of liquid or gas.

2. Description of Related Art

Due to the transmission characteristic of flexural plate waves (FPW) in liquid, i.e. the energy propagation of flexural plate waves is restricted in liquid, flexural plate waves are used for liquid sensors nowadays. Conventional FPW components are made substantially by using silicon as substrates, forming piezoelectric films on there, and finally performing an etching process on the same. However, in practical applications, it is difficult to control the characteristics of multi-layer films, and the characteristics of piezoelectric films are the important parameters that determine the performance of the FPW components. Furthermore, the structure of the piezoelectric films is fragile. Hence, the FPW components are easily broken.

In U.S. Pat. No. 5,212,988, a layer structure made of a piezoelectric material is proposed to produce symmetric or asymmetric Lamb waves. In this design, a ground electrode layer is needed. U.S. Pat. No. 5,212,988 shows another case of conventional FPW components, which are made by using film-depositing and silicon-etching processes. Furthermore, in U.S. Pat. No. 6,688,158, a sacrificial layer micromachining process is used to make components with small areas for formation of arrays, and the components are made of a piezoelectric material, such as aluminum nitride, zinc oxide, or lead zirconium titanate.

In the literature, in "Vapor recognition with an integrated array of polymer-coated flexural plate wave sensors," Volume 62, pp. 121-130, in 2000, Qing-Yun Caiz et al propose a FPW structure, which has a silicon plate as substrate and a piezoelectric film as an actuator. This FPW structure can be designed to form an array structure combined with a measuring system. It is used mainly for recognition of gas.

In the literature, in "Microfabricated Lamb wave device based on PZT Sol-Gel thin film for mechanical transport of solid particles and liquids," Journal of Microelectro-mechanical, Volume 73, pp. 112-123, in 2001, Philippe Luginbuhl et al. propose a FPW structure to illustrate the mechanical transport of solid particles and liquids caused by FPW. However, the sensing results obtained in fluids are not demonstrated.

SUMMARY OF THE INVENTION

An objective of the present invention is to provide an acoustic wave sensing device integrated with micro-channels and a method for the same. In the present invention, a novel manufacturing process and design are proposed for fabrication of acoustic wave sensing devices with a good piezoelectric characteristic, a stable temperature compensation property, and a robust structure. By using the manufacturing process and design of the present invention, the techniques of flexural plate waves can be applied for liquid sensors. The present invention uses a piezoelectric substrate with a thinner portion serving as a sensing area and formed via a mechanical grinding process or a chemical etching process. An inter-digital transducer is provided on the thinner portion of the piezoelectric substrate to produce flexural plate waves. The micro-channels can be formed together with the thinner portion via the same manufacturing process or integrated into the acoustic wave sensing device via linkage.

For achieving the objective above, the present invention provides an acoustic wave sensing device, including a piezoelectric substrate, an inter-digital transducer, and a protective layer. The piezoelectric substrate is made of quartz, lithium niobate or lithium tantalate. It has a thinner portion with a thickness smaller than a wavelength of a propagated acoustic wave and that meets a requiring boundary conditions of producing a flexural plate wave (FPW). The thinner portion is formed via a micromaching process or a chemical process. The thinner portion of the piezoelectric substrate is used for propagation of acoustic waves or stress waves, and for sensing gas or particles in liquid.

The inter-digital transducer is disposed on an upper side or a lower side of the thinner portion of the piezoelectric substrate. The inter-digital transducer has a first electrode and a second electrode made of metal. A propagation path located between the first electrode and the second electrode is coated with a sensing material to form a sensing area. The protective layer is made of macromolecule polymer and coated on the first electrode and the second electrode. However, the protective layer doesn't cover the sensing area, so it doesn't affect the sensing function of the sensing area.

Furthermore, the acoustic wave sensing device further includes a micro-channel formed on the sensing area via the micromaching process or the chemical process. In the present invention, the micro-channels can be formed together with the thinner portion of the piezoelectric substrate via the same manufacturing process or integrated into the piezoelectric substrate via bounding technique. In this way, the present invention can provide an acoustic wave sensor with the integration of micro-channels and at least two acoustic wave sensing devices mentioned above.

For achieving the objective above, the present invention also provides a method for manufacturing the acoustic wave sensing device. It includes steps as follows. First, a piezoelectric substrate is provided and formed with a thinner portion that has a thickness smaller than a wavelength of a propagated acoustic wave and meets boundary conditions of producing FPW. The thinner portion is formed via a one-sided or two-sided mechanical grinding or chemical etching process.

Subsequently, an inter-digital transducer is formed on the thinner portion of the piezoelectric substrate. The inter-digital transducer has a first electrode and a second electrode. If the one-sided process is adopted in the previous step, the inter-digital transducer can be provided on an upper surface or a lower surface of the thinner portion of the piezoelectric substrate or on both of them.

After that, a sensing material is coated on a propagation path located between the electrodes of the inter-digital transducer to form a sensing area. The sensing material can be coated on the surface with or without the inter-digital transducer, or on both of them. Then, a protective layer is coated on the electrodes of the inter-digital transducer.

The method described above can further include a step of forming a micro-channel on the sensing area of the piezoelectric substrate via a mechanical grinding process or a chemical etching process. In this way, an acoustic wave sensing device integrated with a micro-channel is provided. The thinner portion of the piezoelectric substrate and the micro-channel can be formed at the same time.

Numerous additional features, benefits and details of the present invention are described in the detailed description, which follows.

BRIEF DESCRIPTION OF THE DRAWINGS

The foregoing aspects and many of the attendant advantages of this invention will be more readily appreciated as the same becomes better understood by reference to the following detailed description, when taken in conjunction with the accompanying drawings, wherein.

DETAILED DESCRIPTION OF PREFERRED EMBODIMENTS

Figure 1A:
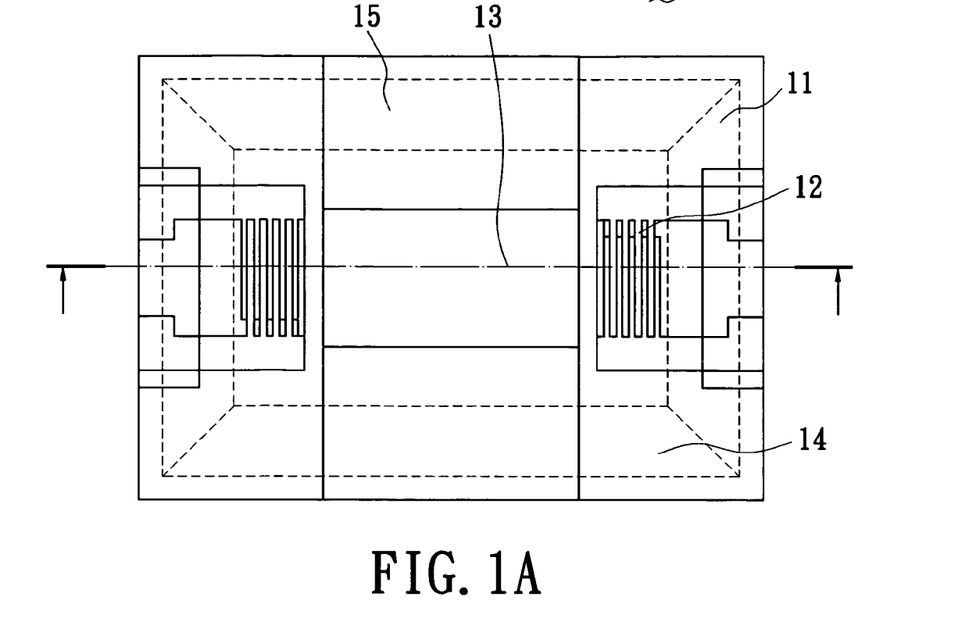
FIG. 1A is a top view of an acoustic wave sensing device integrated with a micro-channel and processed via a one-sided etching process in accordance with the present invention.
Figure 1B:
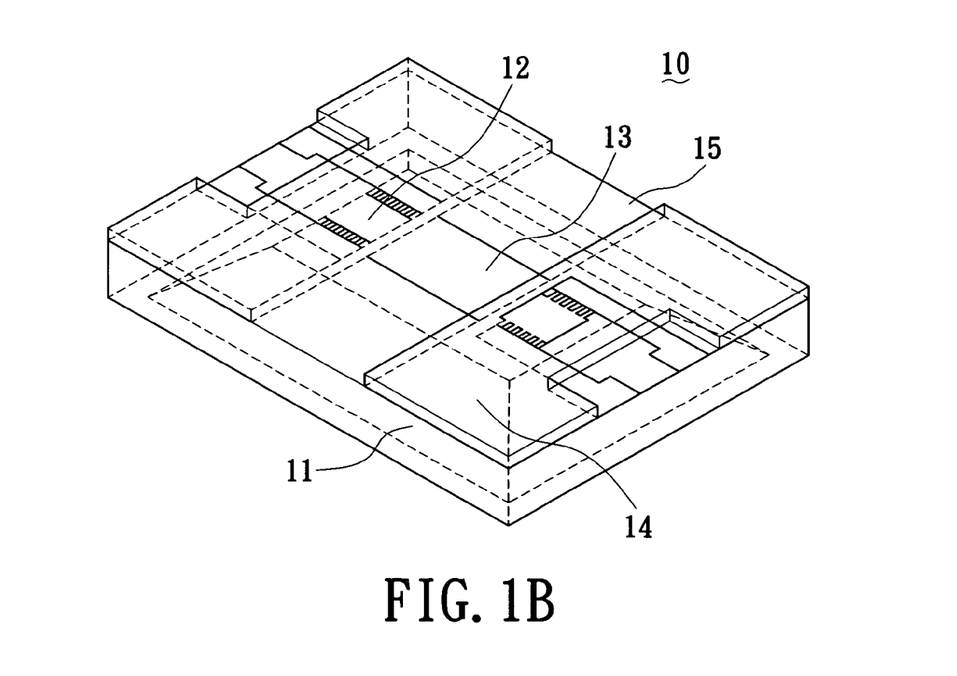
FIG. 1B is an elevation view of the acoustic wave sensing device processed via the one-sided etching process in accordance with the present invention.
Figure 1C:
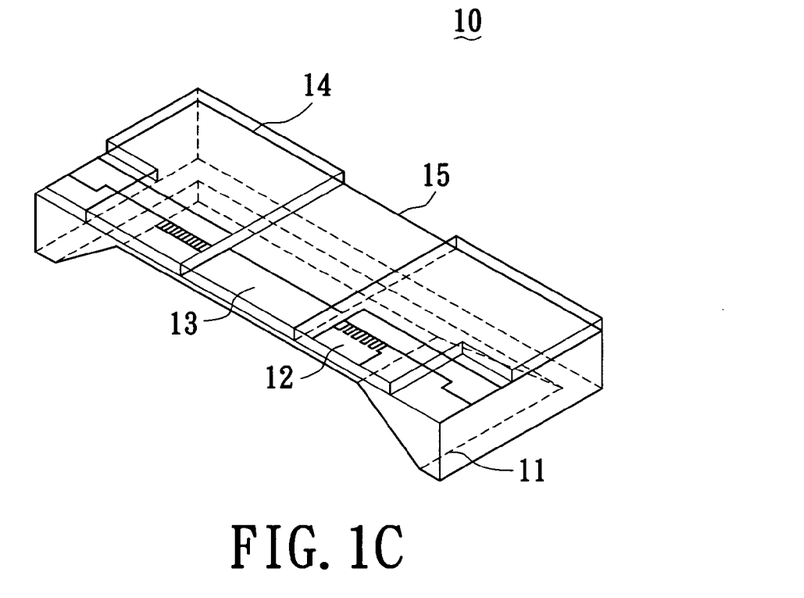
FIG. 1C is a cross-sectional elevation view of the acoustic wave sensing device processed via the one-sided etching process in accordance with the present invention.

Reference is made to FIGS. 1A-C, which are schematic diagrams of an acoustic wave sensing device integrated with micro-channels and made via a one-sided etching process in accordance with the present invention. The acoustic wave sensing device 10 has a piezoelectric substrate 11 with a thinner portion whose thickness is smaller than a wavelength of a transmitted acoustic wave. The thinner portion of the piezoelectric substrate 11 can be formed via a mechanical grinding process or a chemical etching process (a hard mask made of gold and electroplated by nickel can be used in the etching process). It is made to fit in with a vibration condition and boundary conditions for propagation of flexural plate waves (also called Lamb waves). The thinner portion of the piezoelectric substrate 11 is used for propagation of acoustic waves or stress waves. In this way, the piezoelectric substrate 11 can sense acoustic waves of liquid particles or gas particles according to a phase change that occurs in the wave propagation, or a resonant frequency shift when the piezoelectric substrate 11 serves as an oscillator. The advantage of using the piezoelectric substrate 11 is that, compared with the conventional piezoelectric films, the piezoelectric substrate 11 has a better stability in temperature compensation and has a higher electromechanical coupling coefficient. The actuation efficiency of acoustic waves depends on the electromechanical coupling coefficient.

In general, the manufacture of the piezoelectric substrate 11 is difficult because, for example, the piezoelectric substrate 11 is difficult to etch, and handling the roughness of sensing surface and etching rate of the piezoelectric substrate 11 is slow. Hence, the piezoelectric substrate 11 of the present invention is realized by using a quartz as substrate. The quartz crystal has excellent performance in temperature compensation, and thus frequency shifts caused by temperature changes could be overcomed. In practice, the quartz crystal can be replaced by a lithium niobate crystal or a lithium tantalate crystal.

The Inter-digital transducer 12 is disposed on an upper surface or a lower surface of the thinner portion of the piezoelectric substrate 11. The Inter-digital transducer 12 has a first electrode and a second electrode. The characteristics of inter-digital transducer 12, such as the frequency response, are changed according to the parameters of the Inter-digital transducer 12, such as the length spacing. The first and second electrodes are made of metal and a propagation path located between the first and second electrodes is coated with a sensing material to form a sensing area 13. The sensing area 13 is used to sense liquid or gas particles.

The acoustic wave sensing device 10 further has a protective layer 14 for protection of the electrodes. The protective layer 14 is made of polymer and coated on the first and second electrodes of the inter-digital transducer 12. The sensing area 13 is not covered by the protective layer 14.

Moreover, the acoustic wave sensing device 10 has a micro-channel 15 formed on the sensing area via a mechanical etching process or a chemical etching process.

Figure 2A:
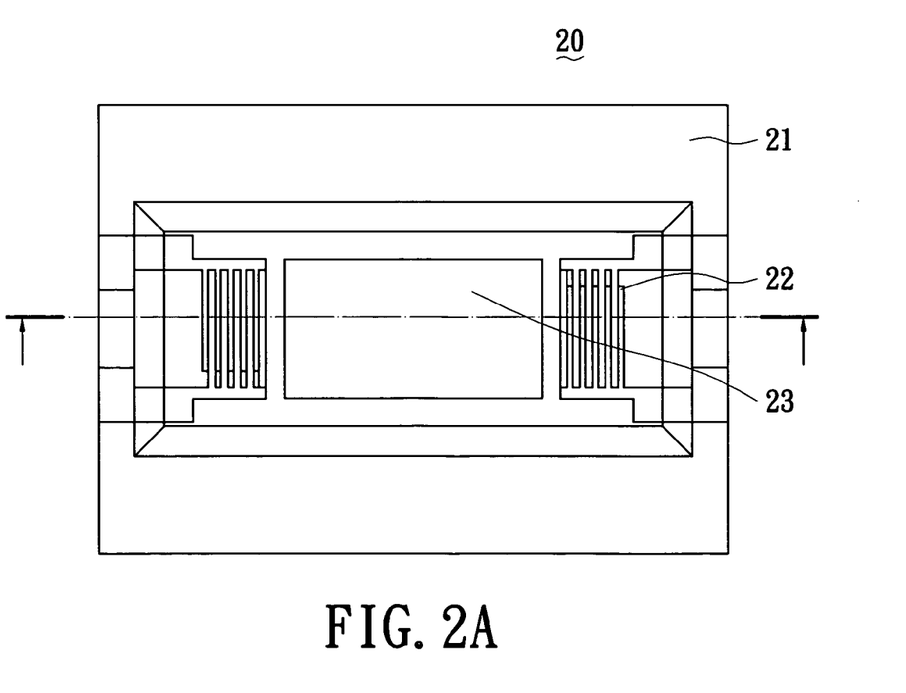
FIG. 2A is a top view of an acoustic wave sensing device processed via a two-sided etching process in accordance with the present invention.
Figure 2B:
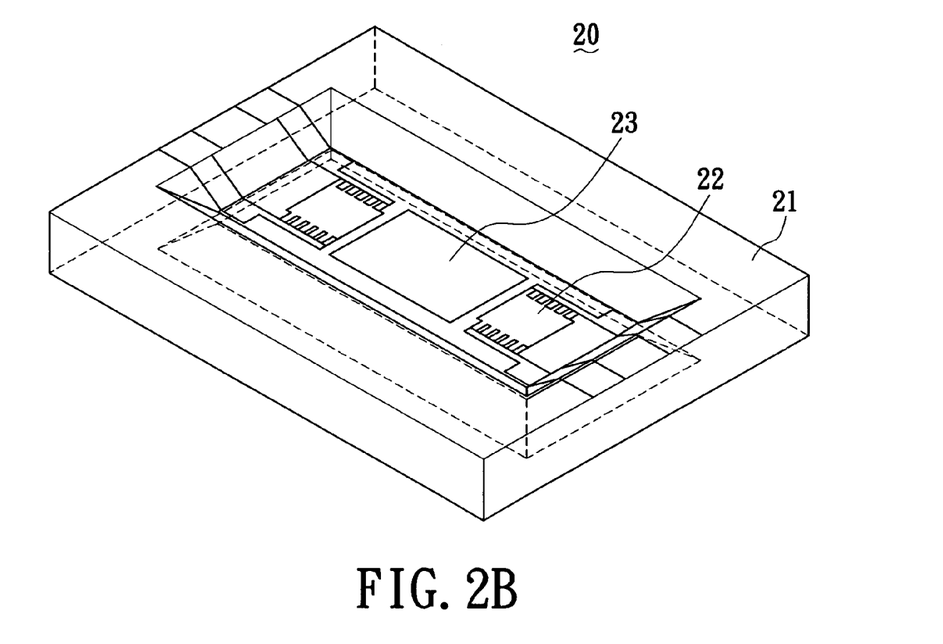
FIG. 2B is an elevation view of the acoustic wave sensing device processed via the two-sided etching process in accordance with the present invention.
Figure 2C:
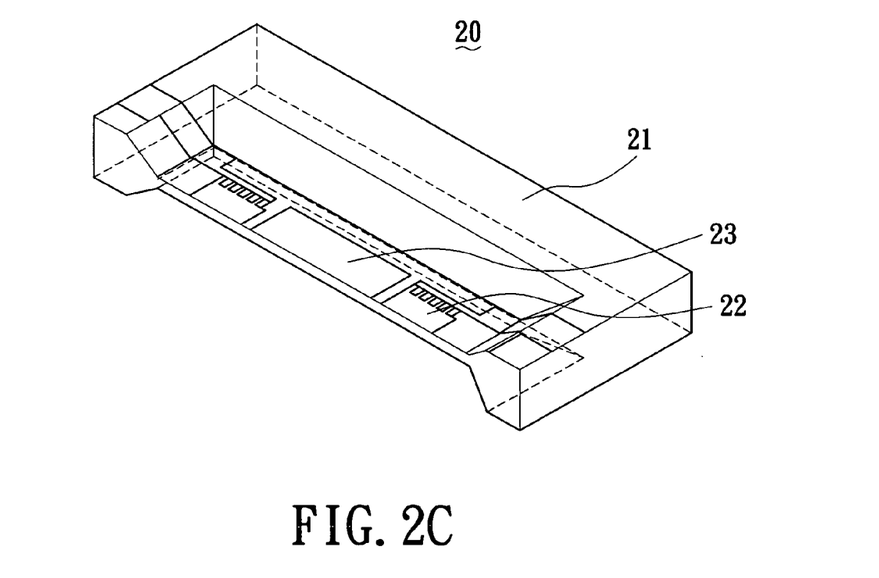
FIG. 2C is a cross-sectional elevation view of the acoustic wave sensing device processed via the two-sided etching process in accordance with the present invention.
Figure 2D:
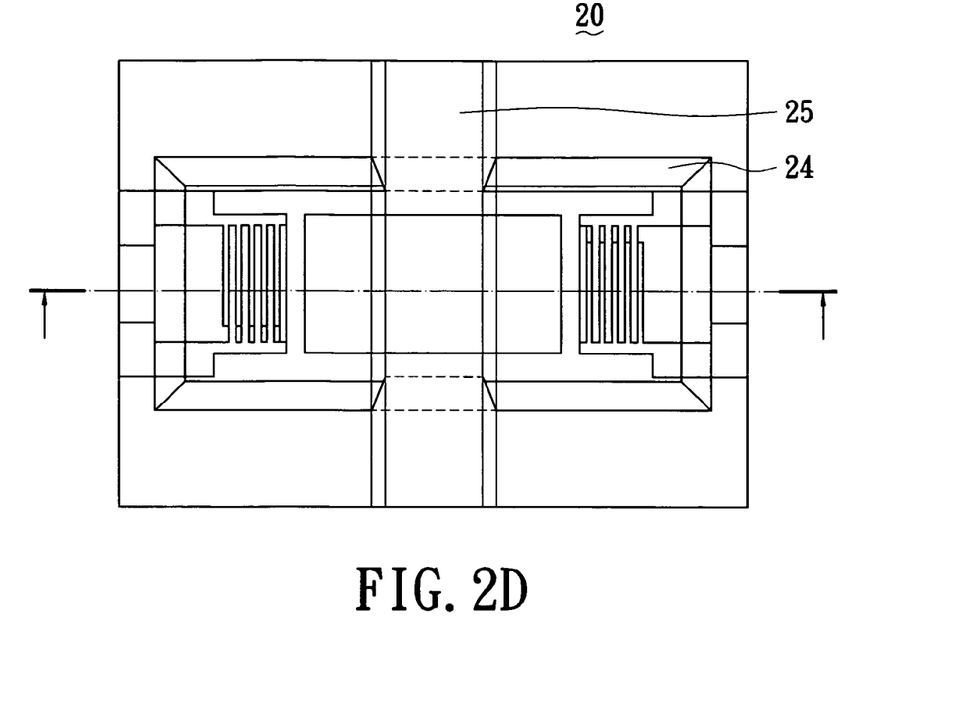
FIG. 2D is a top view of an acoustic wave sensing device processed via the two-sided etching process and integrated with micro-channels in accordance with the present invention.
Figure 2E:
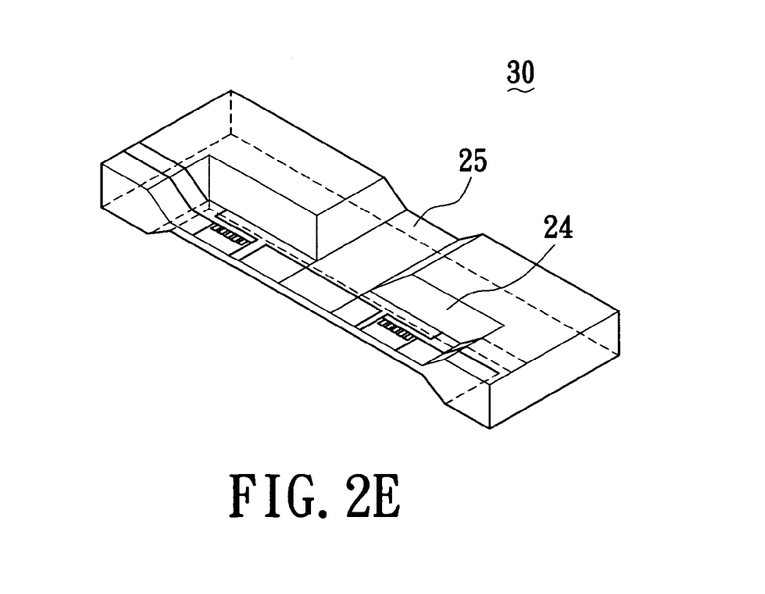
FIG. 2E is a cross-sectional elevation view of the acoustic wave sensing device processed via the two-sided etching process and integrated with micro-channels in accordance with the present invention.

In addition to the acoustic wave sensing device etched in a single side, for development of dip-type manufacturing techniques or increase of manufacturing efficiency, an acoustic wave sensing device made via a two-sided etching process is also provided in the present invention. Reference is made to FIGS. 2A-C, which are schematic diagrams of an acoustic wave sensing device 20 made via the two-sided etching process in accordance with the present invention. Similarly, referring to FIGS. 2D-E, the sensing area 23 of the acoustic wave sensing device 20 that fits in with the requirements of producing flexural plate waves has a micro-channel 25 formed on there. The micro-channel 25 can be formed via a mechanical etching process or a chemical etching process.

Figure 3A:
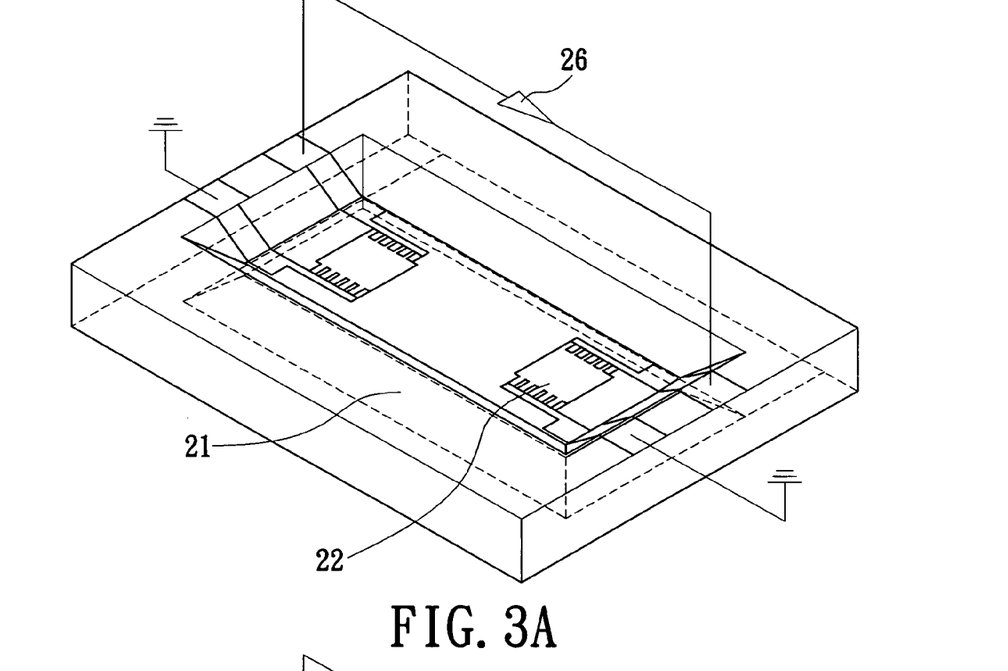
FIG. 3A is an elevation view of an acoustic wave sensing device processed via a two-sided etching process in accordance with the present invention.
Figure 3B:
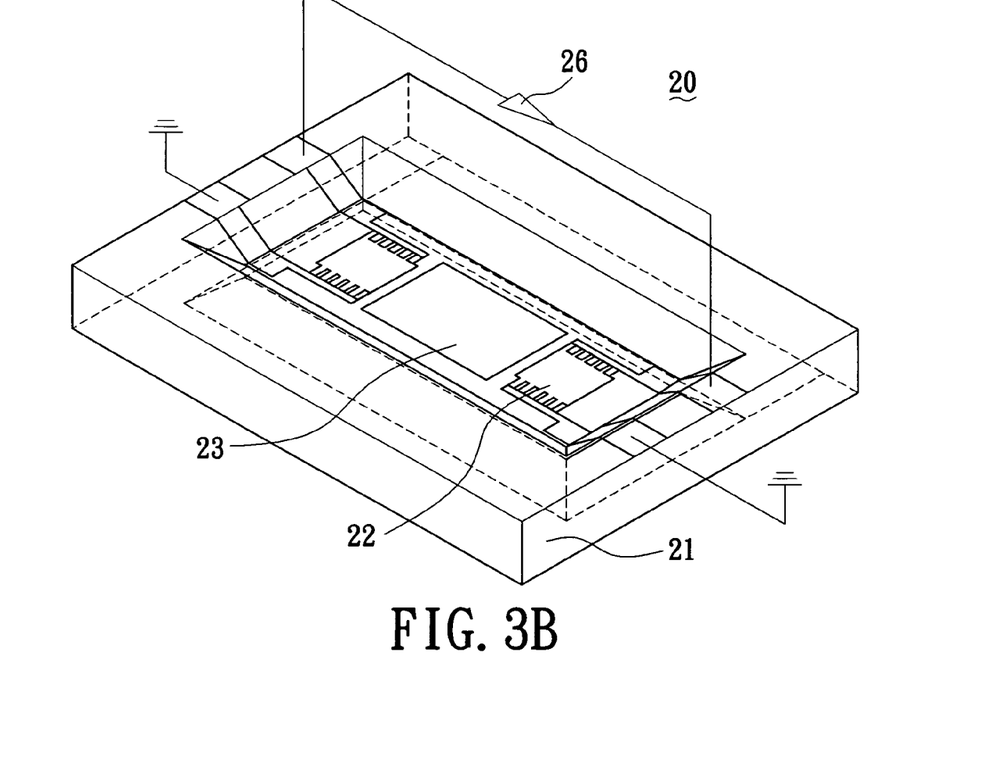
FIG. 3B is an elevation view of an acoustic wave sensing device processed via the two-sided etching process and having a sensing layer in accordance with the present invention.

For sensing acoustic waves, a sensing device is designed to form a structure as shown in FIG. 3A. For avoidance of some undesired factors that affect the overall performance, an acoustic wave sensing device 20 with a sensing area is also provided as shown in FIG. 3B. In the techniques of sensing acoustic waves, because the energy of the flexural plate waves is not lost during propagation when the speed of the flexural plate waves is smaller than that of the liquid waves, the acoustic wave sensing devices 10 and 20 of the present invention is more sensitive in the applications of liquid sensing than the conventional devices. For applications of fluid sensing, the interface affections of the acoustic wave sensing devices 10 and 20 should be taken into consideration. The sensing circuit 26 is used to measure frequency shifts or phase changes of the propagation wave.

Figure 4A:
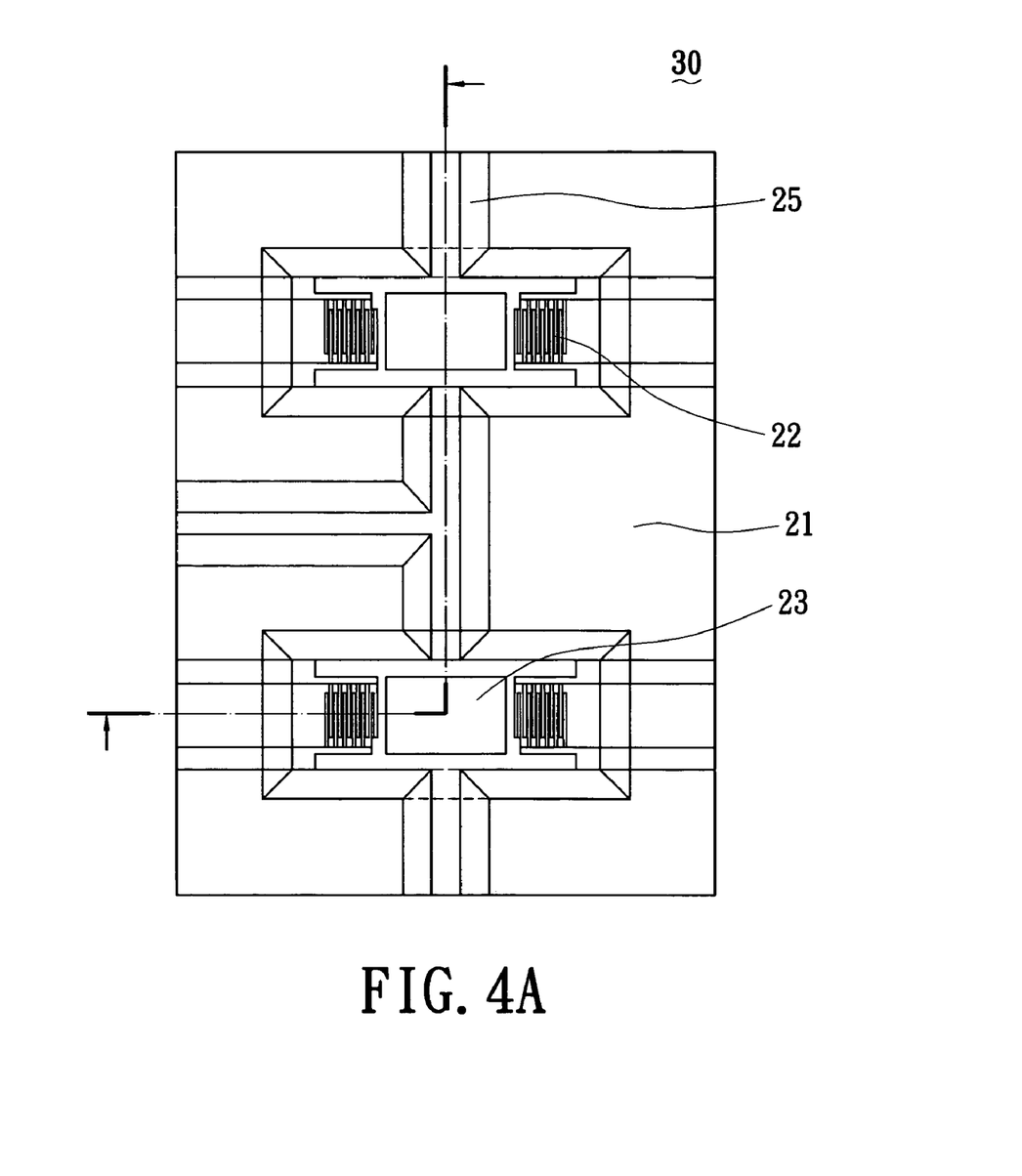
FIG. 4A is a top view of acoustic wave sensors integrated with micro-channels in accordance with the present invention.
Figures 4B, 4C:
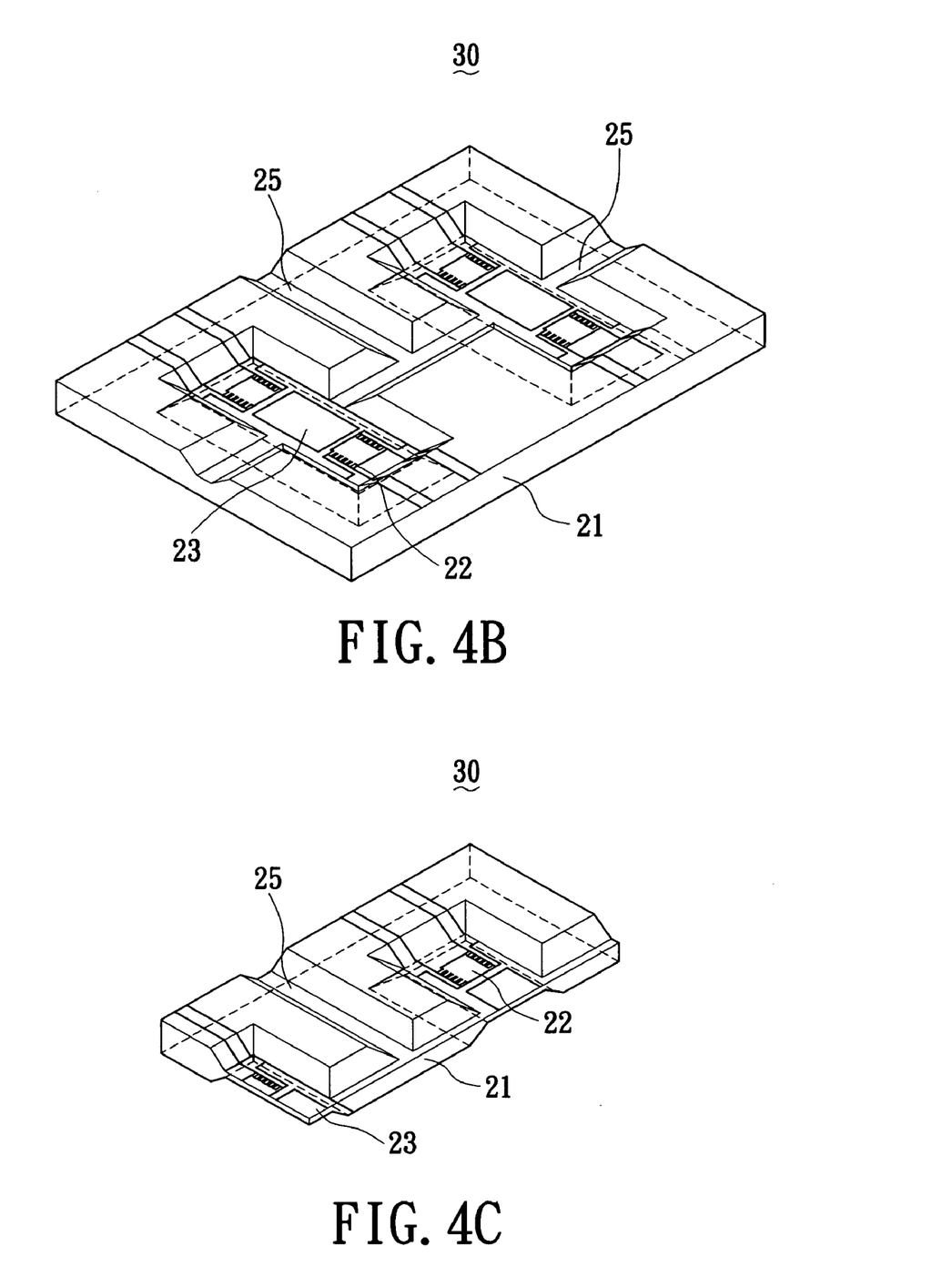
FIG. 4B is an elevation view of acoustic wave sensors integrated with the micro-channels in accordance with the present invention.
FIG. 4C is a cross-sectional elevation view of acoustic wave sensors integrated with the micro-channels in accordance with the present invention.

In the case of two-sided etching, reference is made to FIGS. 4A-C. In addition to the acoustic wave sensing device 20 being made directly by using a piezoelectric substrate 21, in the present invention, multiple micro-channels 25 that can be formed via the same manufacturing process are also provided. Hence, the micro-channels 25 can be easily formed on the piezoelectric substrate 21. In this way, an acoustic wave sensing chip (or an acoustic wave sensing sensor) 30 having micro-channels 25 and an array including at least two acoustic wave sensing devices 20 can be provided. The array of acoustic wave sensing devices 20 is formed on the same piezoelectric substrate 21 in this embodiment. However, in practice, multiple acoustic wave sensing devices can be combined to form an acoustic wave sensing sensor via linkage.

Figure 5:
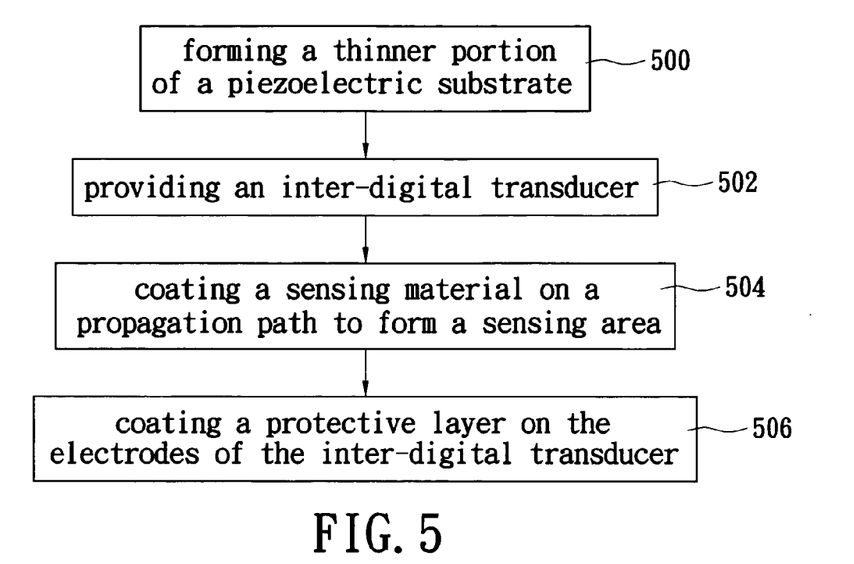
FIG. 5 is a flow chart showing a manufacturing method of the acoustic wave sensing device in accordance with the present invention.

Reference is made to FIG. 5, which is a flow chart showing a manufacturing method of the acoustic wave sensing device in accordance with the present invention. The manufacturing method of the acoustic wave sensing device 10 or 20 includes steps as follows.

First, a one-sided or two-sided mechanical grinding or chemical etching process is used to make a portion of the piezoelectric substrate 11 or 21 thinner and have a thickness smaller than the wavelength of the propagated acoustic waves. The thinner portion of the piezoelectric substrate 11 or 21 thereby meets the requirements for producing flexural plate waves (step 500).

Subsequently, an inter-digital transducer 12 or 22 is provided on the thinner portion of the piezoelectric substrate 11 or 21 (step 502). The inter-digital transducer 12 or 22 includes a first electrode and a second electrode. Furthermore, if the one-sided etching process is adopted in step 500, the inter-digital transducer 12 can be provided on the upper side, the lower side, or both sides of the thinner portion of the piezoelectric substrate 11.

A sensing material is next coated on a propagation path located between the electrodes of the inter-digital transducer 12 or 22 to form a sensing area 13 or 23. The sensing material can be coated on the side with or without the inter-digital transducer 12 or 22 or on both sides (step 504). Finally, a protective layer 14 or 24 is coated on the first and second electrodes of the inter-digital transducer 12 or 22. The protective layer 14 or 24 doesn't cover the sensing area 13 or 23 (step 506).

Figure 6:
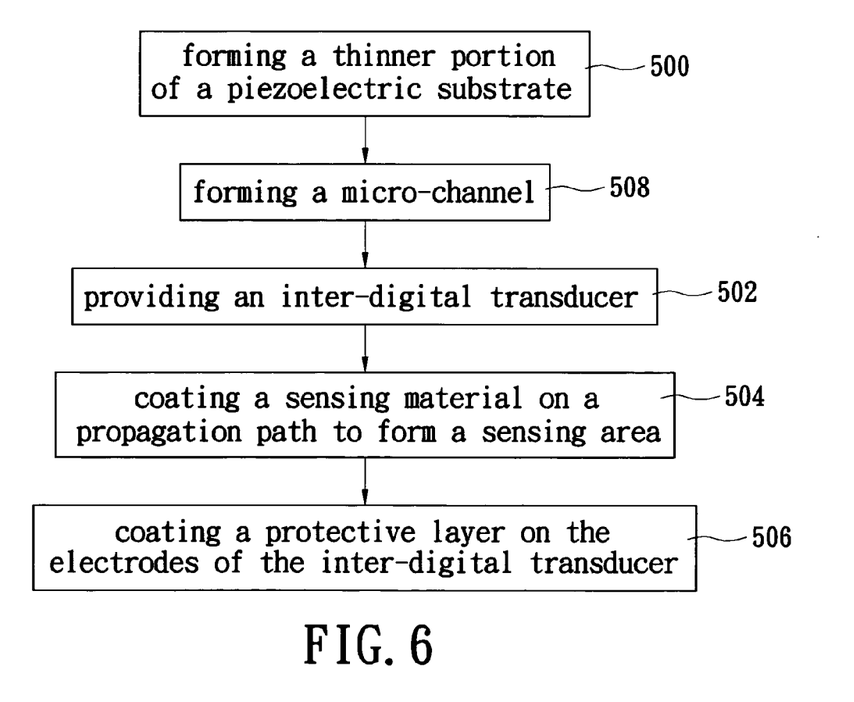
FIG. 6 is a flow chart showing a manufacturing method of the acoustic wave-sensing device integrated with micro-channels in accordance with the present invention.

Reference is made to FIG. 6, which is a flow chart showing a manufacturing method of the acoustic wave sensing device integrated with micro-channels in accordance with the present invention. In order to provide the micro-channels, step 508 is included. After step 506 is performed, the sensing area 13, which fits in with the requirements of producing flexural plate waves, is formed with a micro-channel 15 or micro-channels 25 via a mechanical grinding or chemical etching process (step 508). In this way, the acoustic wave sensing device integrated with micro-channels is provided. In addition, step 500 and step 508 can be performed at the same time.

The present invention provides an acoustic wave sensing device integrated with micro-channels and a method for the same. In the present invention, a novel manufacturing process and design are proposed for fabrication of the acoustic wave sensing devices with a good piezoelectric characteristic, a stable temperature compensation property, and a robust structure. By using the manufacturing process and design of the present invention, the techniques of flexural plate waves can be applied for liquid sensors. In particular, through a two-sided etching process, the substrate is formed with two depressions and the central portions can be formed with films.

The design of the micro-channels is useful for directing a fluid into the sensing area and thus the speed of the reaction that occurs between the sensing films and the fluid under test is increased. Moreover, the micro-channels can also connect to other external components. The present invention can be applied for biochemical tests and form an array of sensing devices, which can obtain sensing results simultaneously.

Although the present invention has been described with reference to the preferred embodiments thereof, it will be understood that the invention is not limited to the details thereof. Various substitutions and modifications have been suggested in the foregoing description, and others will occur to those of ordinary skill in the art. Therefore, all such substitutions and modifications are embraced within the scope of the invention as defined in the appended claims.

What is claimed is:

1. An acoustic wave sensing device, comprising:
   a piezoelectric substrate having a thicker portion and a thinner portion with a thickness smaller than a wavelength of a propagated acoustic wave and meeting a requirement for producing a flexural plate wave (FPW), wherein the thinner portion is formed via a micromachining process or a chemical process;
   an inter-digital transducer disposed on an upper side or a lower side of the thinner portion of the piezoelectric substrate, the inter-digital transducer having a first electrode and a second electrode, wherein a propagation path located between the first electrode and the second electrode is coated with a sensing material capable of sensing liquid or gas particles and provides a sensing area;
   a protective layer coated on the first electrode and the second electrode; and
   a micro-channel that receives gas or liquid, the micro-channel being formed on the sensing area via the micromachining process or the chemical process.

2. The acoustic wave sensing device as claimed in claim 1, wherein the thinner portion of the piezoelectric substrate is used for propagation of the acoustic wave, thus sensing gas particles or liquid particles.

3. The acoustic wave sensing device as claimed in claim 1, wherein the piezoelectric substrate is made of quartz, lithium niobate, or lithium tantalate.

4. The acoustic wave sensing device as claimed in claim 1, wherein the micromachining process used to form the thinner portion of the piezoelectric substrate is a mechanical grinding process.

5. The acoustic wave sensing device as claimed in claim 1, wherein the chemical process used to form the thinner portion of the piezoelectric substrate is a chemical etching process.

6. The acoustic wave sensing device as claimed in claim 1, wherein the micromachining process or the chemical process used to form the thinner portion of the piezoelectric substrate is a one-sided process or a two-sided process.

7. The acoustic wave sensing device as claimed in claim 1, wherein the inter-digital transducer is made of metal.

8. The acoustic wave sensing device as claimed in claim 1, wherein the protective layer is made of a molecular layer or a polymer layer.

9. The acoustic wave sensing device as claimed in claim 1, wherein the chemical process used to form the micro-channel is a chemical etching process.

10. The acoustic wave sensing device as claimed in claim 1, wherein the micromaching process used to form the micro-channel is a mechanical grinding process.

11. An acoustic wave sensor, including at least two units, wherein each unit is identical to the acoustic wave sensing device claimed in claim 1.

12. The acoustic wave sensor as claimed in claim 11, wherein the units are fabricated on the same piezoelectric substrate.

13. The acoustic wave sensor as claimed in claim 11, wherein the units are combined via a linkage.

14. The acoustic wave sensing device as claimed in claim 1, wherein the piezoelectric substrate is substantially rectangular and has first, second, third, and fourth sides, wherein the propagation path is substantially parallel to the first and second sides, or alternatively parallel to the third and fourth sides, and accordingly, wherein the micro-channel extends from the third side of the piezoelectric substrate to the fourth side thereof, or from the first side to the second side thereof.

15. A method for manufacturing an acoustic wave sensing device, comprising:
   thinning a portion of a piezoelectric substrate to provide the piezoelectric substrate with a thicker portion and a thinner portion, wherein the thinner portion has a thickness smaller than a wavelength of a propagated acoustic wave and meets a requirement for producing a FPW;
   forming an inter-digital transducer on the thinner portion of the piezoelectric substrate;
   coating a sensing material capable of sensing liquid or gas particles on a propagation path located between electrodes of the inter-digital transducer to form a sensing area;
   coating a protective layer on the electrodes of the inter-digital transducer; and
   forming a micro-channel on the piezoelectric substrate to receive gas or liquid, including on the sensing area.

16. The method as claimed in claim 15, wherein the piezoelectric substrate is made of quartz, lithium niobate, or lithium tantalate.

17. The method as claimed in claim 15, wherein the thinner portion of the piezoelectric substrate is formed via a mechanical grinding process.

18. The method as claimed in claim 15, wherein the thinner portion of the piezoelectric substrate is formed via a chemical etching process.

19. The method as claimed in claim 15, wherein the thinner portion of the piezoelectric substrate is formed via one-sided process or a two-sided process.

20. The method as claimed in claim 19, wherein if the one-sided process is adopted, the inter-digital transducer is provided on an upper side or a lower side of the thinner portion of the piezoelectric substrate, or on both the upper side and the lower side.

21. The method as claimed in claim 15, wherein the inter-digital transducer is made of metal.

22. The method as claimed in claim 15, wherein the inter-digital transducer has a first electrode and a second electrode.

23. The method as claimed in claim 15, wherein the sensing material is coated on a surface with or without the inter-digital transducer, or on both the surface with the inter-digital transducer and the surface without the inter-digital transducer.

24. The method as claimed in claim 15, wherein the protective layer is made of molecule layer or polymer layer.

25. The method as claimed in claim 15, wherein the micro-channel, is formed via a chemical etching process.

26. The method as claimed in claim 15, wherein the micro-channel is formed via a mechanical grinding process.

27. The method as claimed in claim 15, wherein the micro-channel and the thinner portion of the piezo electric substrate are formed simultaneously.

28. The method as claimed in claim 15, wherein the piezoelectric substrate is substantially rectangular and has first, second, third, and fourth sides, wherein the propagation path is substantially parallel to the first and second sides, or alternatively parallel to the third and fourth sides, and accordingly, wherein the micro-channel extends from the third side of the piezoelectric substrate to the fourth side thereof, or from the first side to the second side thereof.

* * * * *